(12) United States Patent
Buschmann et al.

(10) Patent No.: US 7,507,705 B2
(45) Date of Patent: Mar. 24, 2009

(54) METHODS FOR THE MODULATION OF NEOVASCULARIZATION AND/OR THE GROWTH OF COLLATERAL ARTERIES AND/OR OTHER ARTERIES FROM PREEXISTING ARTERIOLAR CONNECTIONS

(75) Inventors: Ivo R. Buschmann, Bad Nauheim (DE); Wolfgang Schaper, Bad Nauheim (DE)

(73) Assignee: Max-Planck-Gesellschaft Zur Förderung Der Wissenschaften E.V., Berlin (DE)

( * ) Notice: Subject to any disclaimer, the term of this patent is extended or adjusted under 35 U.S.C. 154(b) by 0 days.

(21) Appl. No.: 09/509,764

(22) PCT Filed: Oct. 1, 1998

(86) PCT No.: PCT/EP98/06233

§ 371 (c)(1),
(2), (4) Date: Oct. 16, 2000

(87) PCT Pub. No.: WO99/17798

PCT Pub. Date: Apr. 15, 1999

(65) Prior Publication Data

US 2003/0147862 A1 Aug. 7, 2003

(30) Foreign Application Priority Data

Oct. 2, 1997 (EP) .................................. 97117155

(51) Int. Cl.
*A61K 38/00* (2006.01)
*A01N 37/18* (2006.01)
*A61K 31/70* (2006.01)
*A01N 43/04* (2006.01)

(52) U.S. Cl. .......................................... 514/2; 530/350
(58) Field of Classification Search .................... 514/44; 424/85.1; 435/320.1, 455
See application file for complete search history.

(56) References Cited

U.S. PATENT DOCUMENTS

| | | | | |
|---|---|---|---|---|
| 5,047,504 A | * | 9/1991 | Boone | 530/351 |
| 5,466,781 A | * | 11/1995 | Dorin et al. | 530/351 |
| 5,980,887 A | * | 11/1999 | Isner et al. | 424/93.7 |
| 6,121,246 A | * | 9/2000 | Isner | 514/44 |
| 6,544,543 B1 | | 4/2003 | Mandrusov et al. | |
| 6,592,862 B1 | * | 7/2003 | Schaper et al. | 424/85.1 |
| 2004/0141946 A1 | | 7/2004 | Schäebitz et al. | |
| 2005/0142102 A1 | | 6/2005 | Schäebitz et al. | |

FOREIGN PATENT DOCUMENTS

| | | |
|---|---|---|
| AU | B-77663/87 | 3/1990 |
| EP | 0 258 817 A2 | 3/1988 |
| EP | 0 321 201 A2 | 6/1989 |
| EP | 0 291 533 B1 | 10/1995 |
| EP | 0 451 261 B1 | 1/1996 |
| EP | 0 360 257 B1 | 11/1996 |
| JP | 5-246885 | 9/1993 |
| JP | 5-506673 | 9/1993 |
| JP | 7-188048 | 7/1995 |
| JP | 2001-503427 | 3/2001 |
| WO | WO 85/04188 | 9/1985 |
| WO | WO 89/07654 | 8/1989 |
| WO | WO 92/14480 A1 | 9/1992 |
| WO | WO 94/29469 | 12/1994 |
| WO | WO 95/21864 | 8/1995 |
| WO | WO 97/00957 | 1/1997 |
| WO | WO 97/14307 | 4/1997 |
| WO | WO 98/19712 A1 | 5/1998 |
| WO | WO 98/20027 * | 5/1998 |
| WO | WO 98/33917 | 8/1998 |
| WO | WO 98/44953 | 10/1998 |
| WO | WO 99/17798 | 4/1999 |
| WO | WO 00/60054 | 10/2000 |

OTHER PUBLICATIONS

Rudinger; Characteristics of the amino acids as components of a peptide hormone sequence, 1976, Peptide Hormones.*

(Continued)

*Primary Examiner*—Quang Nguyen
(74) *Attorney, Agent, or Firm*—Sterne, Kessler, Goldstein & Fox P.L.L.C.

(57) ABSTRACT

Described is the modulation of the neovascularization and/or growth of collateral arteries and/or other arteries from preexisting arteriolar connections. Methods are provided for enhancing neovascularization and/or the growth of collateral arteries and/or other arteries from preexisting arteriolar connections comprising contacting organs, tissue or cells with a colony stimulating factor (CSF) or a nucleic acid molecule encoding a CSF. Furthermore, the use of a CSF or a nucleic acid molecule encoding a CSF for the preparation of pharmaceutical compositions for enhancing neovascularization and/or collateral growth of collateral arteries and/or other arteries from preexisting arteriolar connections is described. Also provided are methods for the treatment of tumors comprising contacting an organ, tissue or cells with an agent which suppresses neovascularization and/or the growth of collateral arteries and/or other arteries from preexisting arteriolar connections through the inhibition of the biological activity of CSFs. Described is further the use of an agent which suppresses neovascularization and/or the growth of collateral arteries and/or other arteries from preexisting arteriolar connections through inhibition of the biological activity of CSFs for the preparation of pharmaceutical compositions for the treatment of tumors.

9 Claims, 6 Drawing Sheets

OTHER PUBLICATIONS

Ngo et.al.; Computational Complexity, Protein Structure Prediction, and the Levinthal Paradox, 1994, Protein Folding Problem and Tertiary Structure Prediction:491-494.*

Verma et.al.; Gene therapy- promises, problems and prospects, 1997, Nature, Vil. 389: 239-242.*

Miller et.al.; Targeted vectors for gene therapy, 1995, FASEB J> 9: 190-199.*

Deonarain; Ligand-targeted receptor-mediated vectors for gene delivery, 1998, Exp. Opin. Ther. Patents 8(1): 53-69.*

Mallet et al. Ticlopidine and fatal aplastic anemia in an elderly woman. Ann. Pharmacother. 28:1169-1171, 1994.*

Yoshimura et al. Human monocyte chemoattractant protein-1 (MCP-1). FEB 244:487-493, 1989.

Scholz et al. Arteriogenesis, a new concept of vascular adaptation in occlusive disease. Angiogenesis 4:247-257, 2001, abstract.

Buschmann et al. GM-CSF: a strong arteriogenic factor acting by amplification of monocyte function. Atherosclerosis 159;343-356, 2001, abstract.

American Society of Clinical Oncology, "Update of Recommendations for the Use of Hematopoietic Colony-Stimulating Factors: Evidence-Based, Clinical Practice Guidelines," *ASCO Online*, http://www.asco.org/prof/pp/html/guide/csfq/m_csfq.htm, accessed Jul. 18, 2002, adopted by the American Society of Clinical Oncology Mar. 28, 1996.

Buschmann, I., and Schaper, W., "The pathophysiology of the collateral circulation (arteriogenesis)," *J. Pathol.* 190:338-342, John Wiley & Sons, Ltd. (Feb. 2000).

Carmeliet, P., "Mechanisms of angiogenesis and arteriogenesis," *Nat. Med.* 6:389-395, Nature America Inc. (Mar. 2000).

Deindl, E., et al., "Role of Ischemia and of Hypoxia-Inducible Genes in Arteriogenesis After Femoral Artery Occlusion in the Rabbit," *Circ. Res.* 89:779-786, Lippincott Williams & Watkins (Oct. 2001).

Williams, G.T., et al., "Haemopoietic colony stimulating factors promote cell survival by suppressing apoptosis," *Nature* 343:76-79. Macmillan Journals Ltd. (1990).

Buschmann, I.R., et al., "Therapeutic Induction of Arteriogenesis in Hypoperfused Rat Brain Via Granulocyte-Macrophage Colony-Stimulating Factor," *Circulation* 108:1-6, Lippincott, Williams & Wilkins (Jul. 2003).

Haelens, A., et al., "Leukocyte Migration and Activation by Murine Chemokines," *Immunobiol.* 195:499-521, Gustav Fischer Verlag (Oct. 1996).

Hershey, J.C., et al., "Vascular endothelial growth factor stimulates angiogenesis without improving collateral blood flow following hindlimb ischemia in rabbits," *Heart Vessels* 18:142-149, Springer-Verlag (Jul. 2003).

Luster, A.D., et al., "Chemokines—Chemotactic Cytokines That Mediate Inflammation," *New Engl. J. Med.* 338:436-445, Massachusetts Medical Society (Feb. 1998).

Pipp, F., et al., "Chronically Increased Fluid shear stress following arteriovenous fistula enhances collateral artery growth in a chronic pig hind limb model," *FASEB J.* 17:A497, Abstract No. 338.7, The Federation of American Societies for Experimental Biology (Mar. 2003).

Schotz, D., et al., "Contribution of Arteriogenesis and Angiogenesis to Postocclusive Hindlimb Perfusion in Mice," *J. Mol. Cell. Cardiol.* 34:775-787, Elsevier Science Ltd. (Jul. 2002).

Baffour, R., et al., "Enhanced angiogenesis and growth of collaterals by in vivo administration of recombinant basic fibroblast growth factor in a rabbit model of acute lower limb ischemia: Dose-response effect of basic fibroblast growth factor," *J. Vasc. Surg.* 16:181-191, Mosby-Year Book (1992).

Bussolino, F., et al., "In Vitro and In Vivo Activation of Endothelial Cells by Colony-stimulating Factors," *J. Clin. Invest.* 87:986-995, American Society for Clinical Investigation (1991).

Horiuchi, T., and Weller, P.F., "Expression of Vascular Endothelial Growth Factor by Human Eosinophils: Upregulation by Granulocyte Macrophage Colony-stimulating Factor and Interleukin-5," *Am. J. Respir. Cell. Mol. Biol.* 17:70-77, American Lung Association (Jul. 1997).

Schaper, W., "Angiogenesis in the adult heart," *Basic Res. Cardiol.* 86(Suppl. 2):51-56, Steinkopff Verlag (1991).

Schmidt, R.F., and Thews, G., "Size of the capillary exchange surface," *Physiologie des Menschen*, 24th Edition, Springer-Verlag, Berlin, Germany, p. 528 (1990).

Sunderkötter, C., et al., "Macrophaghe-Derived Angiogenesis Factors," *Pharmac. Ther.* 51:195-216, Pergamon Press (1991).

Sunderkötter, C., et al., "Macrophages and angiogenesis," *J. Leukoc. Biol.* 55:410-422, Society for Leukocyte Biology (1994).

Takeshita, S., et al., "Intramascular Administration of Vascular Endothelial Growth Factor Induces Dose-Dependent Collateral Artery Augmentation in a Rabbit Model of Chronic Limb Ischemia," *Circulation* 90[part 2]: II228-II234, American Heart Association (1994).

Partial English Translation of Schmidt, R.F., and Thews, G., "Size of the capillary exchange surface," *Physiologie des Menschen*, 24th Edition, Springer-Verlag, Berlin, Germany, p. 528 (1990) (Document AS37).

Anderson, W.F., "Human Gene Therapy," *Science* 256:808-813, American Association for the Advancement of Science (1992).

Banerjee, A., et al., "Omega Amino Acids in Peptide Design: Incorporation into Helices," *Biopolymers* 39:769-777, John Wiley and Sons, Inc. (Dec. 1996).

Bates, S. and Vousden, K.H., "p53 in signaling checkpoint arrest or apoptosis," *Curr. Opin. Genet. Dev.* 6:12-19, Current Biology Ltd. (Feb. 1996).

Berks, A.H., "Patent information in biotechnology," *Trends Biotechnol .* 12:352-364, Elsevier Science Ltd. (1994).

Berry, A. and Brenner, S.E., "A prototype computer system for *de novo* protein design," *Biochem. Soc. Trans.* 22:1033-1036, Portland Press Ltd. (1994).

Bauters, C., et al., "Physiological assessment of augmented vascularity induced by VEGF in ischemic rabbit hindlimb," *Am. J. Physiol. Heart Circ. Physiol* 267:H1263-H1271, American Physiological Society (1994).

Bendel, A.E., et al., "A Recombinant Fusion Toxin Targeted to the Granulocyte-Macrophage Colony-Stimulating Factor Receptor," *Leuk. Lymphoma* 25:257-270, Harwood Academic Publishers (Apr. 1997).

Benkirane, N., et al., "Exploration of Requirements for Peptidomimetic Immune Recognition," *J. Biol. Chem.* 271:33218-33224, The American Scoiety for Biochemistry and Molecular Biology, Inc. (Dec. 1996).

Bishayi, B. and Samanta, A.K., "Identification and Characterization of Specific Receptor for Interleukin-8 from the Surface of Human Monocytes," *Scand. J. Immunol.* 43:531-536, Blackwell Science Ltd. (May 1996).

Buschmann, I., et al., "GM-CSF Promotes Collateral Artery Growth Via Prolongation of Macrophage Survival," *J. Mol. Cell. Cardiol.* 30:A126, Academic Press Inc. (Mar. 1998).

Bussolini, F., et al., "Granulocyte- and granulocyte-macrophage-colony stimulating factors induce human endothelial cells to migrate and proliferate," *Nature* 337:471-473, Macmillan Magazines Ltd. (1989).

Calos, M.P., "The potential of extrachromosomal replicating vectors for gene therapy," *Trends Genet.* 12:463-466, Elsevier Science Ltd. (Nov. 1996).

"Chemokine receptors," *Immunology Today Suppl*:26-27, Elsevier Science (Oct. 1996).

Colbère-Garapin, F., et al., "A New Dominant Hybrid Selective Marker for Higher Eukaryotic Cells," *J. Mol. Biol.* 150:1-14, Academic Press Inc. (1981).

Demetri, G.D. and Antman, K.H.S., "Granulocyte-Macrophage Colony-Stimulating Factor (GM-CSF):Preclinical and Clinical Investigations," *Semin. Oncol.* 19:362-385, W.B. Saunders Company (1992).

Dexter, T.M., "Granulocyte Colony Stimulating Factor: From Laboratory Bench to Clinical Use," *Eur. J. Cancer* 30A:S15-S19, Pergamon Press (1994).

Dörner, B., et al., "The Synthesis of Peptidomimetic Combinatorial Libraries Through Successive Amide Alyklations," *Bioorg. Med. Chem.* 4:709-715, Pergamon Press (May 1996).

Eischen, A., et al., "Long term cultures of human monocytes in vitro," *J. Immunol. Meth.* 143:209-221, Elsevier Science Publishers B.V. (1991).

Fassina, G. and Melli, M., "Identification of Interactive Sites of Proteins and Protein Receptors by Computer-Assisted Searches for Complementary Peptide Sequences," *Immunomethods* 5:114-120, Academic Press, Inc. (1994).

Ferrara, N., et al., "Molecular and Biological Properties of the Vascular Endothelial Growth Factor Family of Proteins," *Endocrine Rev.* 13:18-32, The Endocrine Society (1992).

Finn, P.J., et al., "Synthesis and properties of DNA-PNA chimeric oligomers," *Nucl. Acids Res.* 24:3357-3363, Oxford University Press (Sep. 1996).

Gaertner, H.F., et al., Construction of Protein Analogues by Site-Specific Condensation of Unprotected Fragments, *Bioconjugate Chem.* 3:262-268, American Chemical Society (1992).

Gibbs, J.B. and Oliff, A., "Pharmaceutical Research in Molecular Oncology," *Cell* 79:193-198, Cell Press (1994).

Giordano, F.J., et al., "Intracoronary gene transfer of fibroblast growth factor-5 increases blood flow and contractile function in an ischemic region of the heart," *Nat. Med.* 2:534-539, Macmillan Magazines Ltd. (May 1996).

Görge, G., et al., "Microvascular and collateral adaptation in swine hearts following progressive coronary artery stenosis," *Basic Res. Cardiol.* 84:524-535, Steinkopff Verlag (1989).

Han, S.W., et al., "Cloning and expression of the cDNA encoding rat granulocyte colony-stimulating factor," *Gene* 175:101-104, Elsevier Science B.V. (Oct. 1996).

Hartman, S.C. and Mulligan, R.C., "Two dominant-acting selectible markers for gene transfer studies in mammalian cells," *Proc. Natl. Acad. Sci. USA* 85:8047-8051, National Academy of Sciences (1988).

Hoedemakers, R.M.J., et al., "Proliferation of Rat Liver Macrophages *In Vitro*: Influence of Hematopoietic Growth Factors," *Hepatology* 13:666-674, W.B. Saunders Company (1994).

Hoffman, D.L., et al., "Rapid protein structure classification using one-dimensional structure profiles on the BioSCAN parallel computer," *Comput. Appl. Biosci.* 11:674-679, Oxford University Press (1995).

Holloway, C.J., "Applications of Recombinant DNA Technology in the Production of Glycosylated Recombinant Human Granulocyte Colony Stimulating Factor," *Eur. J. Cancer* 30A:S2-S6, Pergamon Press (1994).

Hupp, T.R., et al., "Small Peptides Activate the Latent Sequence-Specific DNA Binding Function of p53," *Cell* 83:237-245, Cell Press (1995).

Isner, J.M., et al., "Clinical evidence of angiogenesis after arterial gene transfer of phVEGF$_{165}$ in patient with ischemic limb," *Lancet* 348:370-374, The Lancet Ltd. (Aug. 1996).

Ito, W.D., et al., "Monocyte Chemotactic Protein-1 Increases Collateral and Peripheral Conductance After Femoral Artery Occlusion," *Circ. Res.* 80:829-837, American Heart Association, Inc. (Jun. 1997).

Itoh, S., "Production of human G-CSF and its derivatives by recombinant DNA technology," *Tanpakushitsu Kakusan Koso* 35:2620-2631, Kyoritsu Shuppan Company Limited (1990).

Jakeman, L.B., et al., "Binding Sites for Vascular Endothelial Growth Factor Are Localized on Endothelial Cells in Adult Rat Tissues,'' *J. Clin. Invest.* 89:244-253, The Rockefeller University Press (1992).

Jensen, K.K., et al., "Kinetics for Hybridization of Peptide Nucleic Acids (PNA) with DNA and RNA Studied with the BIAcore Technique," *Biochem.* 36:5072-5077, American Chemical Society (Apr. 1997).

Klagsbrun, M. and D'Amore, P.A., "Regulators of Angiogenesis," *Ann. Rev. Physiol.* 53:217-239, Annual Reviews Inc. (1991).

Kluck, P.M.C., et al., "Order of human hematopoietic growth factor and receptor genes on the long arm of chromosome 5, as determined by fluorescence in situ hybridization," *Ann. Hematol.* 66:15-20, Springer-Verlag (1993).

Koch, T., et al., "Improvements in automated PNA synthesis using Boc/Z monomers," *J. Pept. Res.* 49:80-88, Munksgaard (Jan. 1997).

Kogut, M.H., et al., "Neutralization of G-CSF Inhibits ILK-Induced Heterophil Influx," *Inflammation* 21:9-25, Plenum Press (Feb. 1997).

Kothari, S.S., et al., "Expression of Granulocyte Colony Stimulating Factor (G-CSF) and Granulocyte/Macrophage Colony Stimulating Factor (GN-CSF) mRNA upon Stimulation with Phorbol Ester," *Blood Cells. Mol. Dis.* 21:192-200, The Blood Cells Foundation (1995).

Leung, D.W., et al., "Vascular Endothelial Growth Factor Is a Secreted Angiogenic Mitogen," *Science* 246:1306-1309, American Association for the Advancement of Science (1989).

Lieschke, G.J. and Burgess, A.W., "Granulocyte Colony-Stimulating Factor and Granulocyte-Macrophage Colony-Stimulating Factor," *N. Engl. J. Med.* 327:28-35, Massachussetts Medical Society (1992).

Lieschke, G.J. and Burgess, A.W., "Granulocyte Colony-Stimulating Factor and Granulocyte-Macrophage Colony-Stimulating Factor," *N. Engl. J. Med.* 327:99-106, Massachussetts Medical Society (1992).

Lopez, A.F., et al., "Recombinant Human Granulocyte-Macrophage Colony-stimulating Factor Stimulates In Vitro Mature Human Neutrophil and Eosinophil Function, Surface Receptor Expression, and Survival," *J. Clin. Invest.* 78:1220-1228, The Rockefeller University Press (1986).

Lowy, I., et al., "Isolation of Transforming DNA: Cloning the Hamster aprt Gene," *Cell* 22:817-823, Massachussetts Institute of Technology (1980).

Lu, H.S., et al., "Isolation and Characterization of Three Recombinant Human Granulocyte Colony Stimulating Factor His → Gln Isoforms Produced in *Escherichia coli*," *Prot. Express. Purif.* 4:465-472, Academic Press, Inc. (1993).

Malmborg, A.-C. and Borrebaeck, C.A.K., "BIAcore as a tool in antibody engineering," *J. Immunol. Meth.* 183:7-13, Elsevier Science B.V. (1995).

Mangan, D.F. and Wahl, S.M., "Differential Regulation of Human Monocyte Programmed Cell Death (Apoptosis) by Chemotactic Factors and Pro-Inflammatory Cytokines," *J. Immunol.* 147:3408-3412, The American Association of Immunologists (1991).

Matsushime, H., "Macrophage Cell Cylce Control by M-CSF/CSF-1," *Rinsho Ketsueki* 36:406-409, Japan Society of Clinical Hematology (1995).

Millauer, B., et al., "High Affinity VEGF Binding and Developmental Expression Suggest Flk-1 as a Major Regulator of Vasculogenesis and Angiogenesis," *Cell* 72:835-846, Cell Press (1993).

Milner, J., "DNA damage, p53 and anticancer therapies," *Nat. Med.* 1:879-880, Macmillan Magazines Ltd. (1995).

Monge, A., et al., "Computer Modeling of Protein Folding: Conformational and Energetic Analysis of Reduced and Detailed Protein Models," *J. Mol. Biol.* 247:995-1012, Academic Press Ltd. (1995).

Mülhauser, J., et al., "VEGF$_{165}$ Expressed by a Replication-Deficient Recombinant Adenovirus Vector Induces Angiogenesis In Vivo," *Circ. Res.* 77:1077-1086, American Heart Association, Inc. (1995).

Mulligan, R.C. and Berg, P., "Selection for animal cells that express the *Escherichia coli* gene coding for xanthine-guanine phosphoribosyltransferase," *Proc. Natl. Acad. Sci. USA* 78:2072-2076, National Academy of Sciences (1981).

Munn, D.H. and Cheung, N.-K.V., "Antibody-independent phagocytosis of tumor cells by human monocyte-derived macrophages cultured in recombinant macrophage colony-stimulating factor," *Cancer Immunol. Immunother.* 41:46-52, Springer-Verlag (1995).

Naito, M., et al., "Macrophage Differentiation and Granulomatous Inflammation in Osteopetrotic Mice (op/op) Defective in the Production of CSF-1," *Mol. Reprod. Dev.* 46:85-91, Wiley-Liss, Inc. (Jan. 1997).

O'Hare, K., et al., "Transformation of mouse fibroblasts to methotrexate resistance by a recombinant plasmid expressing a prokaryotic dihydrofolate reductase," *Proc. Natl. Acad. Sci. USA* 78:1527-1531, National Academy of Sciences (1981).

Olszewski, K.A., et al., "Folding Simulations and Computer Redesign of Protein A Three-Helix Bundle Motifs," *Proteins* 25:286-299, Wiley-Liss, Inc. (Jul. 1996).

Ostresh, J.M., et al., "Generation and Use of Nonsupport-Bound Peptide and Peptidomimetic Combinatorial Libraries," *Meth. Enzymol.* 267:220-234, Academic Press, Inc. (May 1996).

Pabo, C.O. and Suchanek, E.G., "Computer-Aided Model-Building Strategies for Protein Design," *Biochem.* 25:5987-5991, American Chemical Society (1986).

Paskins-Hurlburt, A.J. and Hollenberg, N.K., "'Tissue Need' and Limb Collateral Arterial Growth," *Circ. Res.* 70:546-553, American Heart Association, Inc. (1992).

Pasyk, S., et al., "DNA synthesis in coronary collaterals after coronary artery occlusion in conscious dog," *Am. J. Physiol.* 242:H1031-H1037, American Physiological Society (1982).

Perentesis, J.P., et al., "Granulocyte-Macrophage Colony-Stimulating Factor Receptor-Targeted Therapy of Chemotherapy- and Radiation-Resistant Human Myeloid Leukemias," *Leuk. Lympoma* 25:247-256, Harwood Academic Publishers (Apr. 1997).

Peters, K.G., et al., "Vascular endothelial growth factor receptor expression during embryogenesis and tissue repair suggests a role in endothelial differentiation and blood vessel growth," *Proc. Natl. Acad. Sci. USA* 90:8915-8919, National Academy of Sciences (1993).

Plate, K.H., et al., "Vascular endothelial growth factor is a potential tumour angiogenesis factor in human gliomas *in vivo*, " *Nature* 359:845-848, Macmillan Magazines Ltd. (1992).

Raivich, G., et. al., "Increase of Macrophage Colony-Stimulating Factor and Granulocyte-Macrophage Colony-Stimulating Factor Receptors in the Regenerating Rat Facial Nucleus," *J. Neurosci. Res.* 30:682-686, Wiley-Liss, Inc. (1991).

Renouf, D.V. and Hounsell, E.F., "Molecular Modelling of Glycoproteins by Homology with Non-Glycosylated Protein Domains, Computer Simulated Glycosylation and Molecular Dynamic," in: *Glycoimmunology*. Alavi, A. and Axford, J.S., Eds., Plenum Press, New York, New York, pp. 37-45 (1995).

Rohde, M.F., et al., "Peptide Mapping of Recombinant Proteins," *Dev. Biol. Standard.* 83:121-127, Kerger (1994).

Rose, R.B., et al., "Three-Dimensional Structures of HIV-1 and SIV Protease Product Complexes," *Biochem.* 35:12933-12944, American Chemical Society (Oct. 1996).

Rutenber, E.E., et al., "A New Class of HIV-1 Protease Inhibitor: The Crystallographic Structure, Inhibition and Chemical Synthesis of an Aminimide Peptide Isostere," *Bioorg. Med. Chem.* 4:1545-1558, Pergamon Press (Sep. 1996).

Santerre, R.F., et al., "Expression of prokaryotic genes for hygromycin B and G418 resistance as dominant-selection markers in mouse L cells," *Gene* 30:147-156, Elsevier Science Publishers (1984).

Sasayama, S. and Fujita, M., "Recent Insights Into Coronary Collateral Circulation," *Circ. Res.* 85:1197-1204, American Heart Association, Inc. (1992).

Schaper, W. and Ito, W.D., "Molecular Mechanisms of Coronary Collateral Vessel Growth," *Circ. Res.* 79:911-919, American Heart Association, Inc. (Nov. 1996).

Schaper, W. and Ito, W.D., "Therapeutic targets in cardiovascular disorders," *Curr. Opin. Biotech.* 7:635-640, Current Biology Ltd. (Dec. 1996).

Schier, R. and Marks, J.D., "Efficient *in vitro* affinity maturation of phage antibodies using BIAcore guided selections," *Hum. Antibod. Hybridomas* 7:97-105, Forefront Publishing (1996).

Selgas, R., et al., "Immunomodulation of peritoneal macrophage by granulocyte-macrophage colony-stimulating factor in humans," *Kidney International* 50:2070-2078, Blackwell Science, Inc. (Dec. 1996).

Shimamura, K., et al., "Establishment of Specific Monoclonal Antibodies Against Recombinant Human Granulocyte Colony-Stimulating Factor (hG-CSF) and Their Application for Immunoperoxidase Staining of Paraffin-embedded Sections," *J. Histochem. Cytochem.* 38:283-286, The Histochemical Society (1990).

Steinecke, P. and Schreier, P.H., "Ribozymes," in: *Methods in Cell Biology*. Galbraith, D.W., et al., Eds., Academic Press, Inc., San Diego, California, vol. 50, pp. 449-460 (1995).

Szybalska, E.H. and Szybalski, W., "Genetics of Human Cell Lines, IV. DNA-Mediated Heritable Transformation of a Biochemical Trait," *Proc. Natl. Acad. Sci. USA* 48:2026-2034, National Academy of Sciences (1962).

Takeshita, S., et al., "Therapeutic Angiogenesis," *J. Clin. Invest.* 93:662-670, The Rockefeller University Press (1994).

Tuder, R.M., et al., "Increased Gene Expression for VEGF and the VEGF Receptors *KDR/Flk* and *Flt* in Lungs Exposed to Acute or to Chronic Hypoxia," *J. Clin. Invest.* 95:1798-1807, The Rockefeller University Press (1995).

Vincent, F., et al., "Human Blood-derived Macrophages: Differentiation in vitro of a Large Quantity of Cells in Serum-free Medium," *Exp. Hematol.* 20:17-23, Springer International (1992).

Wang, Q. and Finer, M.H., "Second-generation adenovirus vectors," *Nat. Med.* 2:714-716, Macmillan Magazines Ltd. (Jun. 1996).

Wigler, M., et al., "Transfer of Purified Herpes Virus Thymidine Kinase Gene to Cultured Mouse Cells," *Cell* 11:223-232, Massachussetts Institute of Technology (1977).

Wigler, M., et al., "Transformation of mammalian cells with an amplifiable dominant-acting gene," *Proc. Natl. Acad. Sci. USA* 77:3567-3570, National Academy of Sciences (1980).

Williams, R.S., et al., "Introduction of foreign genes into tissues of living mice by DNA-coated microprojectiles," *Proc. Natl. Acad. Sci. USA* 88:2726-2729, National Academy of Sciences (1991).

Wodak, S.J., "Computer-Aided Design in Protein Engineering," *Ann. NY Acad. Sci.* 501:1-13, New York Academy of Sciences (1987).

Wong, R.L., et al., "Murine T Helper Cell Clones Secrete Granulocyte-Macrophage Colony-Stimulating Factor (GmCSF) by both Interleukin-2-Dependent and Interleukin-2-Independent Pathways," *Cellular Immunity* 123:445-455, Academic Press, Inc. (1989).

Yamasaki, M., et al., "Modification of Recombinant Human Granulocyte Colony-Stimulating Factor (rhG-CSF) and Its Derivative ND 28 with Polyethylene Glycol," *J. Biochemistry* 115:814-819, The Japanese Biochemical Society (1994).

Zhang, Y. L., et al., "A Superactive Peptidomimetic Analog of a Farnesylated Dodecapeptide Yeast Pheromone," *Biochem. Biophys. Res. Comm.* 224:327-331, Academic Press, Inc. (Jul. 1996).

Dialog File 155, PubMed Identifier:1702549, Itoh, S., "Production of G-CSF and its derivatives by recombinant DNA technology," Tanpakushitsu kakusan koso 35:2620-2631, (1990), Record Created Feb. 2, 1991.

Auerbach, R., et al., "Angiogenesis Assays: A Critical Overview, " *Clin. Chem.* 49:32-40, Lange Medical Books/McGraw-Hill (Jan. 2003).

Ganong, W.F., ed., "Section VI. Circulating Body Fluids," in: *Review of Medical Physiology, 22nd Ed.*, Lange Medical Books/McGraw-Hill, New York, NY, pp. 515-518 (Mar. 2005).

Kuhlmann, M.T., et al., "G-CSF/SCF reduces inducible arrhythmias in the infarcted heart potentially via increased connexin43 expression and arteriogenesis," *J. Exp. Med.*, DOI: 10.1084/jem.20051151, 11 pages, (epublished Jan. 2006).

Löms Ziegler-Heitbrock, H.-W., "The biology of the monocyte system," *Eur. J. Cell Biol.* 49:1-12, Wissenschaftliche Verlagsgesellschaft (1989).

Metcalf, D., "The Colony Stimulating Factors. Discovery, Development, and Clinical Applications," *Cancer* 65:2185-2194, Wiley (1990).

Pimentel, E., "Colony-Stimulating Factors," *Ann. Clin. Lab. Sci.* 20:36-55, Institute for Clinical Science, Inc. (1990).

Schneeloch, E., et al., "Granulocyte-macrophage colony-stimulating factor-induced arteriogenesis reduces energy failure in hemodynamic stroke," *Proc. Natl. Acad. Sci. USA* 101:12730-12735, National Academy of Sciences (Aug. 2004).

Seiler, C., et al., "Promotion of Collateral Growth by Granulocyte-Macrophage Colony-Stimulating Factor in Patients with Coronary Artery Disease," *Circulation* 104:2012-2017, Lippincott, Williams & Wilkins (Oct. 2001).

Takagi, Y., et al., "Granulocyte-Colony Stimulating Factor Augments Neovascularization Induced by Bone Marrow Transplantation in Rat Hindlimb Ischemia," *J. Pharmacol. Sci.* 99:45-51, The Japanese Pharmaceutical Society (Dec. 2005).

Arras, M., et al., "Monocyte Activation in Angiogenesis and Collateral Growth in the Rabbit Hindlimb," *J. Clin. Invest.* 101:40-50, The American Society for Clinical Investigation, Inc. (Jan. 1998).

Patent Abstracts of Japan, English language abstract for JP 7-188048, Japanese Patent Office (listed on accompanying PTO/SB/08A as Document AO4).

Unverified English language translation of portion of Japanese First Official Action dated Dec. 27, 2006 for Japanese Patent Application No. 2000-514667, filed Oct. 1, 1998, Japanese Patent Office, 3 pages.

Heard, S.O., et al., "Effect of prophylactic administration of recombinant human granulocyte colony-stimulating factor (filgrastim) on the frequency of nosocomial infections in patients with acute traumatic brain injury or cerebral hemorrhage," *Crit Care Med* 26:748-754, Williams & Wilkins (Apr. 1998).

Hierholzer, C., et al., "Activation of Stat Proteins Following Ischemia Reperfusion Injury Demonstrates a Distinct IL-6 and G-CSF Mediated Profile," *Transplantation Proceedings* 30:2647, Elsevier Science Inc. (Sep. 1998).

U.S. Appl. No. 11/846,699, filed Oct. 31, 2007.
U.S. Appl. No. 11/930,758, filed Oct. 31, 2007.
U.S. Appl. No. 11/931,128, filed Oct. 31, 2007.
U.S. Appl. No. 11/931,295, filed Oct. 31, 2007.
U.S. Appl. No. 11/931,326, filed Oct. 31, 2007.
U.S. Appl. No. 11/931,618, filed Oct. 31, 2007.
U.S. Appl. No. 11/932,383, filed Oct. 31, 2007.

Schäbitz, Wolf-Rüdiger, "Treatment of Acute Ischemic Stroke, with AX200 (G-CSF): Results of the AXIS Study," 23 pages, presented at the 80th meeting of the Deutsche Gesellschaft für Neurologie on Sep. 14, 2007, and available at http://www.sygnis.de/e740/e738/e1254/files1279/AXISBerlinE.pdf.

Minnerup, J. et al., "Meta-Analysis of the Efficacy of Granulocyte-Colony Stimulating Factor in Animal Models of Focal Cerebral Ischemia," *Stroke* 39: 000 - 000, 8 pages, American Heart Association, Inc., DOI: 10.1161/STROKEAHA. 107.506816 (Apr. 10, 2008).

\* cited by examiner

METHODS FOR THE MODULATION OF NEOVASCULARIZATION AND/OR THE GROWTH OF COLLATERAL ARTERIES AND/OR OTHER ARTERIES FROM PREEXISTING ARTERIOLAR CONNECTIONS

BACKGROUND OF THE INVENTION

1. Field of the Invention

The present invention relates generally to the modulation of neovascularization and/or the growth of collateral arteries or other arteries from preexisting arteriolar connections.

2. Related Art

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

In the treatment of subjects with arterial occlusive diseases most of the current treatment strategies aim at ameliorating their effects. The only curative approaches involve angioplasty (balloon dilatation) or bypassing surgery. The former carries a high risk of restenosis and can only be performed in certain arterial occlusive diseases, like ischemic heart disease. The latter is invasive and also restricted to certain kinds of arterial occlusive diseases. There is no established treatment for the enhancement of neovascularization and/or collateral growth.

Vascular growth in adult organisms proceeds via two distinct mechanisms, sprouting of capillaries (angiogenesis) and in situ enlargement of preexisting arteriolar connections into true collateral arteries (Schaper, J. Collateral Circulation—Heart, Brain, Kidney, Limbs. Boston, Dordrecht, London: Kluwer Academic Publishers; 1993). Recent studies have disclosed mechanisms leading to angiogenesis with vascular endothelial growth factor (VEGF) as a major component (Tuder, J. Clin. Invest. 95 (1995), 1798-1807; Plate, Nature 359 (1992), 845-848; Ferrara, Endocrine Reviews 13 (1992), 18-42; Klagsbrun, Annu. Rev. Physiol. 53 (1991), 217-239; Leung, Science 246 (1990), 1306-1309). This specific endothelial mitogen is upregulated by hypoxia and is able to promote vessel growth when infused into rabbit hindlimbs after femoral artery excision (Takeshita, J. Clin. Invest. 93 (1994), 662-670; Bauters, Am. J. Physiol. 267 (1994), H1263-H1271). These studies however did not distinguish between capillary sprouting, a mechanism called angiogenesis, and true collateral artery growth. Whereas VEGF is only mitogenic for endothelial cells, collateral artery growth requires the proliferation of endothelial and smooth muscle cells and pronounced remodeling processes occur (Schaper, J. Collateral Circulation—Heart, Brain, Kidney, Limbs. Boston, Dordrecht, London: Kluwer Academic Publishers; 1993; Jakeman, J. Clin. Invest. 89 (1992), 244-253; Peters, Proc. Natl. Acad. Sci. USA 90 (1993), 8915-8919; Millauer, Cell 72 (1993), 835-846; Pasyk, Am. J. Physiol. 242 (1982), H1031-H1037). Furthermore mainly capillary sprouting is observed in ischemic territories for example in the pig heart or in rapidly growing tumors (Schaper, J. Collateral Circulation— Heart, Brain, Kidney, Limbs. Boston, Dordrecht, London: Kluwer Academic Publishers; 1993; Plate, Nature 359 (1992), 845-848; Bates, Curr. Opin. Genet. Dev. 6 (1996), 12-19; Bates, Curr. Opin. Genet. Dev. 6 (1996), 12-19; Görge, Basic Res. Cardiol. 84 (1989), 524-535). True collateral artery growth, however, is temporally and spacially dissociated from ischemia in most models studied (Schaper, J. Collateral Circulation—Heart, Brain, Kidney, Limbs. Boston, Dordrecht, London: Kluwer Academic Publishers; 1993; Paskins-Hurlburt, Circ. Res. 70 (1992), 546-553). Other or additional mechanisms as those described for angiogenesis in ischemic territories are therefore needed to explain collateral artery growth. From previous studies it is known that these collateral arteries grow from preexisting arteriolar connections (Schaper, J. Collateral Circulation—Heart, Brain, Kidney, Limbs. Boston, Dordrecht, London: Kluwer Academic Publishers; 1993).

However, while agents such as VEGF and other growth factors are presently being employed to stimulate the development of angiogenesis after arterial occlusion, such agents are not envisaged as being capable of modulating the growth of preexisting arteriolar connections into true collateral arteries.

Thus, the technical problem of the present invention is to provide pharmaceutical compositions and methods for the modulation of neovascularization and/or the growth of collateral arteries and/or other arteries from preexisting arteriolar connections.

BRIEF SUMMARY OF THE INVENTION

The solution to this technical problem is achieved by providing the embodiments characterized in the claims.

Accordingly, the invention relates to a method for enhancing the neovascularization and/or the growth of collateral arteries and/or other arteries from preexisting arteriolar connections comprising contacting an organ, tissue or cells with a colony stimulating factor (CSF) or a nucleic acid molecule encoding said CSF.

In particular, the present invention provides a method for enhancing neovascularization and/or the growth of collateral arteries and/or other arteries from preexisting arteriolar connections comprising contacting an organ, tissue or cells with a colony stimulating factor (CSF) or a nucleic acid molecule encoding said CSF. The present invention also relates to the use of a CSF or a nucleic acid molecule encoding said CSF for the preparation of pharmaceutical compositions for enhancing neovascularization and/or collateral growth of collateral arteries and/or other arteries from preexisting arteriolar connections. Furthermore, the present invention relates to a method for the treatment of tumors comprising contacting an organ, tissue or cells with an agent which suppresses neovascularization and/or the growth of collateral arteries and/or other arteries from preexisting arteriolar connections through the inhibition of the biological activity of a CSF. The present invention further involves the use of an agent which suppresses neovascularization and/or the growth of collateral arteries and/or other arteries from preexisting arteriolar connections through the inhibition of the biological activity of a CSF for the preparation of pharmaceutical compositions for the treatment of tumors.

BRIEF DESCRIPTION OF THE DRAWINGS

The figures show

DETAILED DESCRIPTION OF THE INVENTION

The term "neovascularization" within the meaning of the present invention refers to a review of Sasayama, Circulation Res. 85 (1992), 1197-1204.

For the purpose of the present invention the growth of arteries from preexisting arteriolar connections is also called "arteriogenesis". In particular, "arteriogenesis" is the in situ growth of arteries by proliferation of endothelial and smooth muscle cells from preexisting arteriolar connections supplying blood to ischemic tissue, tumor or sites of inflammation. These vessels largely grow outside the affected tissue but are much more important for the delivery of nutrients to the ischemic territory, the tumor or the site of inflammation than capillaries sprouting in the diseased tissue by angiogenic processes.

In the context of the present invention the term "colony stimulating factor (CSF)" refers to proteins and peptides which can act on macrophages and which are capable of promoting collateral artery growth by direct activation, proliferation and/or potentiation of the effector functions of resident and newly-recruited macrophages. Thus, according to the present invention, any CSF or other substances which are functionally equivalent to a CSF, namely which are capable of promoting collateral artery growth can be used for the purpose of the present invention. The action of the CSF employed in the present invention may not be limited to the above-described specificity but they may also act on, for example eosinophils, lymphocyte subpopulations and/or stem cells. Advantageously, the CSF is antiatherogenic.

In accordance with the present invention, it has surprisingly been found that that locally applied Granulocyte-Macrophage-Colony-Stimulating-Factor (GM-CSF) caused a significant increase in collateral artery growth. These results were based on a marked increase of collateral conductance measurements. Peripheral pressures and collateral flows were measured under maximal vasodilation using Statham pressure transducers, fluorescent microspheres and FACS analysis which allowed the calculation of collateral conductances from pressure flow relations. Furthermore, post mortem angiograms revealed a significantly higher number of collateral arteries compared to untreated animals. To the best of the inventors' knowledge, this is the very first report that anti-atherogenic and widely clinical established colony stimulating factors are capable of significantly enhancing neovascularization and/or collateral artery growth and/or the growth of other arteries from preexisting arteriolar connections in vivo. Hence, CSFs that can be employed in accordance with the present invention are particularly suited for the treatment of atheriosclerosis.

Experiments performed within the scope of the present invention demonstrate that local infusion of GM-CSF increases both collateral- and peripheral conductance after femoral artery occlusion due to enhanced vessel growth by its proliferative effects on macrophages. Thus, CSFs or nucleic acid molecules encoding CSFs can be used for the activation and proliferation of macrophages which in turn leads to neovascularization and/or the growth of collateral arteries as well as to growth of arteries from preexisting arteriolar connections, which is needed for the cure of several occlusive diseases. Granulocyte colony stimulating factor (G-CSF) and granulocyte macrophage-colony stimulating factor (GM-CSF) belong to a family of glycoprotidic growth factors required for the survival, growth and differentiation of heamatopoietic precursor cells. Therefore this substance has been used clinically to treat patients with heamatologic and oncologic disorders. The action of these CSF molecules was thought to be restricted to cells of the heamatopoietic origin (Demetri, Semin. Oncol. 19 (1992), 362-385; Lieschke, N. Engl. J. Med. 327(1992), 28-35/Comments 99-106). Furthermore, several studies have demonstrated that these colony stimulating factors also play a major role in lipid metabolism.

Although recent experiments have shown that GM-CSF is able to directly promote a number of macrophage and granulocyte effector functions including cell survival (Selgas, Kidney International 50 (1996), 2070-2078; Lopez, J. Clin. Invest. 78 (1986), 1220-1228; Eischen, J. Immunol. Meth. 147 (1991), 3408-3412; Vincent, Exp. Hematol. 20 (1992), 17-23; Mangan, J Immunol. 147 (1991), 3408-3412), activation, proliferation (Hoedemakers, Hepatology 13 (1994), 666-674; Matsushime, Japanese Journal of Clinical Hematology 36 (1995), 406-409); differentiation (Munn, Cancer Immunology, Immunotherapy 41 (1995), 46-52), and migration of local tissue macrophages (Bussolini, Nature 337 (1989), 471-473) it was not known that GM-CSF or other colony stimulating factors play a role in the development of collateral arteries and arteriogenesis.

The CSFs to be employed in the methods and uses of the present invention may be obtained from various sources described in the prior art; see, e.g., Gaertner, Bioconjugate Chemistry 3 (1992), 262-268; Dexter, European Journal of Cancer 30A (1994), 15-9; Rohde, Developments in Biological Standardization 83 (1994), 121-127; Lu, Protein Expression & Purification 4 (1993), 465-472; Itoh, Tanpakushitsu Kakusan Koso—Protein, Nucleic Acid, Enzyme 35, 2620-2631. The potential exists, in the use of recombinant DNA technology, for the preparation of various derivatives of colony stimulating factor (CSF) comprising a functional part thereof or proteins which are functionally equivalent to CSFs as described above. In this context, as used throughout this specification "functional equivalent or "functional part" of an CSF means a protein having part or all of the primary structural conformation of a CSF possessing at least the biological property of promoting at least one macrophage or granulocyte effector function mentioned above. The functional part of said protein or the functionally equivalent protein may be a derivative of an CSF by way of amino acid deletion(s), substitution(s), insertion(s), addition(s) and/or replacement(s) of the amino acid sequence, for example by means of site directed mutagenesis of the underlying DNA. Recombinant DNA technology is well known to those skilled in the art and described, for example, in Sambrook et al. (Molecular cloning; A Laboratory Manual, Second Edition, Cold Spring Harbor Laboratory Press, Cold Spring Harbor N.Y. (1989)). Modified CSFs are described, e.g., in Yamasaki, Journal of Biochemistry 115 (1994), 814-819.

CSFs or functional parts thereof or proteins which are functionally equivalent to CSFs, may be produced by known conventional chemical syntheses or recombinant techniques employing the amino acid and DNA sequences described in the prior art; see, e.g., EP-A-0 177 568; Han, Source Gene 175 (1996), 101-104; Kothari, Blood Cells, Molecules & Diseases 21 (1995), 192-200; Holloway, European Journal of Cancer 30A (1994), 2-6. For example, CSFs may be produced by culturing a suitable cell or cell line which has been transformed with a DNA sequence encoding upon expression under the control of regulatory sequences a CSF or a functional part thereof or a protein which is functionally equivalent to CSF. Suitable techniques for the production of recombinant proteins are described in, e.g., Sambrook, supra.

Methods for constructing CSFs and proteins as described above useful in the methods and uses of the present invention by chemical synthetic means are also known to those of skill in the art.

In another embodiment, the invention relates to the use of a colony stimulating factor (CSF) or a nucleic acid molecule encoding said CSF for the preparation of a pharmaceutical composition for enhancing neovascularization and/or collateral growth of collateral arteries and/or other arteries from preexisting arteriolar connections.

The pharmaceutical composition comprises at least one CSF as defined above, and optionally a pharmaceutically acceptable carrier or exipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by conventional methods. The pharmaceutical compositions can be administered to the subject at a suitable dose. The dosage regimen may be determined by the attending physician considering the condition of the patient, the severity of the disease and other clinical factors. Administration of the suitable compositions may be effected by different ways, e.g. by intravenous, intraperetoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery.

In a preferred embodiment, said CSF used in the methods and uses of the invention is selected from the group consisting of Granulocyte-Macrophage-Colony-Stimulating Factor (GM-CSF), Granulocyte-Colony-Stimulating Factor (G-CSF), Macrophage-Colony-Stimulating Factor (M-CSF), Colony-Stimulating Factor (CSF-I), functionally equivalent substances or functional derivatives thereof.

In a preferred embodiment, the methods and uses of the invention may be employed for diseases caused by a vascular disease or a cardiac infarct or a stroke or for any disease where an increase of blood supply via collaterals, arteries etc. is needed.

In a particularly preferred embodiment, the methods and uses of the invention are designed to be applied to a subject suffering from arteriosclerosis, a coronary artery disease, a cerebral occlusive disease, a peripheral occlusive disease, a visceral occlusive disease, renal occlusive disease, a mesenterial arterial insufficiency or an ophthamic or retenal occlusion or for any disease where atherosclerotic plaques in the vascular wall lead to an obstruction of the vessel diameter.

In a further preferred embodiment, the methods and uses of the invention are designed to be applied to a subject during or after exposure to an agent or radiation or surgical treatment which damage or destroy arteries.

In a preferred embodiment, the CSF used in the methods and uses of the invention is a recombinant CSF. DNA sequences encoding CSFs which can be used in the methods and uses of the invention are described in the prior art; see, e.g., Holloway, European Journal of Cancer 30A (1994), 2-6 or references cited above. Moreover, DNA and amino acid sequences of CSFs are available in the Gene Bank database. As described above, methods for the production of recombinant proteins are well-known to the person skilled in the art; see, e.g., Sambrook, supra.

In a further preferred embodiment, the method and the use of the present invention is designed to be applied in conjugation with a growth factor, preferably fibroblast growth factor or vascular endothelial growth factor (VEGF). This embodiment is particularly suited for enhancing of both sprouting of capillaries (angiogenesis) and in situ enlargement of preexisting arteriolar connections into true collateral arteries. Pharmaceutical compositions comprising, for example, CSF such as GM-CSF, and a growth factor such as VEGF may be used for the treatment of peripheral vascular diseases or coronary artery disease.

In another preferred embodiment, the method of the invention comprises (a) obtaining cells, tissue or an organ from a subject;
(b) introducing into said cells, tissue or organ a nucleic acid molecule encoding and capable of expressing the CSF in vivo; and
(c) reintroducing the cells, tissue or organ obtained in step (b) into the same subject or a different subject.

It is envisaged by the present invention that the CSFs and the nucleic acid molecules encoding the CSFs are administered either alone or in combination, and optionally together with a pharmaceutically acceptable carrier or exipient. Said nucleic acid molecules may be stably integrated into the genome of the cell or may be maintained in a form extrachromosomally, see, e.g., Calos, Trends Genet. 12 (1996), 463-466. On the other hand, viral vectors described in the prior art may be used for transfecting certain cells, tissues or organs.

Furthermore, it is possible to use a pharmaceutical composition of the invention which comprises a nucleic acid molecule encoding a CSF in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acid molecules to a specific site in the body for gene therapy may also be accomplished using a biolistic delivery system, such as that described by Williams (Proc. Natl. Acad. Sci. USA 88 (1991), 2726-2729).

Standard methods for transfecting cells with nucleic acid molecules are well known to those skilled in the art of molecular biology, see, e.g., WO 94/29469. Gene therapy to prevent or decrease the development of diseases described herein may be carried out by directly administering the nucleic acid molecule encoding a CSF to a patient or by transfecting cells with said nucleic acid molecule ex vivo and infusing the transfected cells into the patient. Furthermore, research pertaining to gene transfer into cells of the germ line is one of the fastest growing fields in reproductive biology. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539;

Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The nucleic acid molecules comprised in the pharmaceutical composition of the invention may be designed for direct introduction or for introduction via liposomes, or viral vectors (e.g. adenoviral, retroviral) containing said nucleic acid molecule into the cell. Preferably, said cell is a germ line cell, embryonic cell, or egg cell or derived therefrom.

It is to be understood that the introduced nucleic acid molecules encoding the CSF express said CSF after introduction into said cell and preferably remain in this status during the lifetime of said cell. For example, cell lines which stably express said CSF may be engineered according to methods well known to those skilled in the art. Rather than using expression vectors which contain viral origins of replication, host cells can be transformed with the recombinant DNA molecule or vector of the invention and a selectable marker, either on the same or separate vectors. Following the introduction of foreign DNA, engineered cells may be allowed to grow for 1-2 days in an enriched media, and then are switched to a selective media. The selectable marker in the recombinant plasmid confers resistance to the selection and allows for the selection of cells having stably integrated the plasmid into their chromosomes and grow to form foci which in turn can be cloned and expanded into cell lines. This method may advantageously be used to engineer cell lines which express a CSF. Such cells may be also be administered in accordance with the pharmaceutical compositions, methods and uses of the invention.

A number of selection systems may be used, including but not limited to the herpes simplex virus thymidine kinase (Wigler, Cell 11(1977), 223), hypoxanthine-guanine phosphoribosyltransferase (Szybalska, Proc. Natl. Acad. Sci. USA 48 (1962), 2026), and adenine phosphoribosyltransferase (Lowy, Cell 22 (1980), 817) in tk$^-$, hgprt$^-$ or aprt$^-$ cells, respectively. Also, antimetabolite resistance can be used as the basis of selection for dhfr, which confers resistance to methotrexate (Wigler, Proc. Natl. Acad. Sci. USA 77 (1980), 3567; O'Hare, Proc. Natl. Acad. Sci. USA 78 (1981), 1527), gpt, which confers resistance to mycophenolic acid (Mulligan, Proc. Natl. Acad. Sci. USA 78 (1981), 2072); neo, which confers resistance to the aminoglycoside G-418 (Colberre-Garapin, J. Mol. Biol. 150 (1981), 1); hygro, which confers resistance to hygromycin (Santerre, Gene 30 (1984), 147); or puromycin (pat, puromycin N-acetyl transferase). Additional selectable genes have been described, for example, trpB, which allows cells to utilize indole in place of tryptophan; hisD, which allows cells to utilize histinol in place of histidine (Hartman, Proc. Natl. Acad. Sci. USA 85 (1988), 8047); and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.).

Thus, in a preferred embodiment, the nucleic acid molecule comprised in the pharmaceutical composition for the use of the invention is designed for the expression of the CSF by cells in vivo by, for example, direct introduction of said nucleic acid molecule or introduction of a plasmid, a plasmid in liposomes, or a viral vector (e.g. adenoviral, retroviral) containing said nucleic acid molecule.

In a preferred embodiment of the method and uses of the present invention, the CSF derivative or functional equivalent substance is an antibody, (poly)peptide, nucleic acid, small organic compound, ligand, hormone, PNA or peptidomimetic.

In this context, it is understood that the CSFs to be employed according to the present invention may be, e.g., modified by conventional methods known in the art. For example, it is possible to use fragments which retain the biological activity of CSFs as described above, namely the capability of promoting collateral artery growth. This further allows the construction of chimeric proteins and peptides wherein other functional amino acid sequences may be either physically linked by, e.g., chemical means to the CSF or may be fused by recombinant DNA techniques well known in the art. Furthermore, folding simulations and computer redesign of structural motifs of the CSFs or their receptors can be performed using appropriate computer programs (Olszewski, Proteins 25 (1996), 286-299; Hoffman, Comput. Appl. Biosci. 11 (1995), 675-679). Computer modeling of protein folding can be used for the conformational and energetic analysis of detailed receptor and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the CSF and its receptor by computer assistant searches for complementary peptide sequences (Fassina, Immunomethods 5 (1994), 114-120). Further appropriate computer systems for the design of protein and peptides are described in the prior art, for example in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used for, e.g., the preparation of peptidomimetics of the CSFs or fragments thereof. Such pseudopeptide analogues of the natural amino acid sequence of the protein may very efficiently mimic the parent protein or peptide (Benkirane, J. Biol. Chem. 271 (1996), 33218-33224). For example, incorporation of easily available achiral $\Omega$-amino acid residues into a CSF protein or a fragment thereof results in the substitution of amide bonds by polymethylene units of an aliphatic chain, thereby providing a convenient strategy for constructing a peptidomimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptidomimetics of CSF may also be identified by the synthesis of peptidomimetic combinatorial libraries through successive amide alkylation and testing the resulting compounds, e.g., according to the methods described in the prior art. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, antibodies or fragments thereof may be employed which, e.g., upon binding to a CSF-receptor mimic the biological activity of a CSF.

Furthermore, a three-dimensional and/or crystallographic structure of the CSF or of its receptor can be used for the design of peptidomimetic inhibitors of the biological activity of a CSF (Rose, Biochemistry 35 (1996), 12933-12944; Rutenber, Bioorg. Med. Chem. 4 (1996), 1545-1558).

As discussed above, neovascularization and the growth of arteries from preexisting arteriolar connections is essential for the delivery of nutrition to tumors. Thus, if the growth of said vessels to the tumor would be suppressed suppression and/or inhibition of tumor growth is to be expected.

Accordingly, the present invention also relates to a method for the treatment of tumors comprising contacting an organ, tissue or cells with an agent which suppresses neovascularization and/or the growth of collateral arteries and/or other arteries from preexisting arteriolar connections through the inhibition of the biological activity of a CSF.

Tumor Macrophages require specific growth factors, e.g., M-CSF/CSF-1, for their proliferation throughout the G1 phase of the cell cycle. Once cells enter S phase, macrophages complete mitosis in the absence of M-CSF/CSF-1. During the G1 phase, cyclin D (a cell cyclus regulator, that together with cyclin dependent kinase (cdk 4) promotes entry of the cell into M-phase (Alberts, Biology of the Cell (1989), Second Edition) is induced by M-CSF/CSF-1 stimulation. The enzymatic activity of cyclin D could be negatively regulated by recently reported inhibitory proteins to determine the timing for entry into S phase in macrophages (Matsushime, Japanese Journal of Clinical Hematology 36 (1995), 406-409).

It could be shown that among CSF-dependent macrophages especially monocytes as well as tissue specific macrophages (in the female reproductive tract) seem to be dependent on CSF-1 for their further differentiation (Maito, Mol. Reprod. Dev. 46 (1997), 85-91). Beyond this GM-CSF/M-CSF are essential for the macrophage survival. Thus, as it could be demonstrated in accordance with the present invention that CSFs promote neovascularization and collateral artery growth withdrawal of these factors should result in inhibition or decrease of neovascularization and/or collateral artery growth and, thus, in the suppression of tumor growth. Agents which suppress neovascularization and/or the growth of collateral arteries and/or other arteries from preexisting arteriolar connections may be peptides, proteins, nucleic acids, antibodies, small organic compounds, hormones, neural transmitters, peptidomimics, or PNAs (Milner, Nature Medicine 1 (1995), 879-880; Hupp, Cell 83 (1995), 237-245; Gibbs, Cell 79 (1994), 193-198). For the preparation and application of such compounds, the person skilled in the art can use the methods known in the art, for example those referred to above.

The present invention further relates to the use of an agent which suppresses neovascularization and/or the growth of collateral arteries and/or other arteries from preexisting arteriolar connections through the inhibition of the biological activity of a CSF for the preparation of a pharmaceutical composition for the treatment of tumors.

In a preferred embodiment, the agent used in the methods and uses of the invention as described above inhibits the biological activity of a CSF and/or inhibits an intracellular signal or signal cascade comprising MAPK and/or JNK/SAPK triggered in macrophages through the receptor for the CSF. Various receptors of CSFs are described in the prior art, for example in Chemokine Receptors. Immunology Today (1996), Suppl S: 26-27; Bendel, Leukemia & Lymphoma 25 (1997), 257-270; Perentesis, Leukemia & Lymphoma 25 (1997), 247-256; Bishay, Scandinavian Journal of Immunology 43 (1996), 531-536; Kluck, Annals of Hematology 66 (1993), 15-20; Raivich, Journal of Neuroscience Research 30 (1991), 682-686 or in Wong, Cellular Immunology 123 (1989), 445-455.

In another preferred embodiment, said receptor is a CSF receptor. Said receptor or specific domains thereof which a responsible for triggering a signal leading to collateral artery growth may be blocked or modulated by methods described herein.

In a preferred embodiment, the agent used in the methods and uses of the invention is a(n) antibody, (poly)peptide, nucleic acid, small organic compound, ligand, hormone, PNA or peptidomimetic.

Nucleic acid molecules specifically hybridizing to CSF encoding genes and/or their regulatory sequences may be used for repression of expression of said gene, for example due to an antisense or triple helix effect or they may be used for the construction of appropriate ribozymes (see, e.g., EP-B1 0 291 533, EP-A1 0 321 201, EP-A2 0 360 257) which specifically cleave the (pre)-mRNA of a gene encoding a CSF. The nucleic and amino acid sequences encoding CSFs are known in the art and described, for example, in Han, Source Gene 175 (1996), 101-104; Kothari, Blood Cells, Molecules & Diseases 21 (1995), 192-200 or in Holloway, European Journal of Cancer 30A (1994), 2-6. Selection of appropriate target sites and corresponding ribozymes can be done as described for example in Steinecke, Ribozymes, Methods in Cell Biology 50, Galbraith et al. eds Academic Press, Inc. (1995), 449-460.

Nucleic acids comprise DNA or RNA or hybrids thereof. Furthermore, said nucleic acid may contain, for example, thioester bonds and/or nucleotide analogues, commonly used in oligonucleotide anti-sense approaches. Said modifications may be useful for the stabilization of the nucleic acid molecule against endo- and/or exonucleases in the cell. Furthermore, the so-called "peptide nucleic acid" (PNA) technique can be used for the inhibition of the expression of a gene encoding a CSF. For example, the binding of PNAs to complementary as well as various single stranded RNA and DNA nucleic acid molecules can be systematically investigated using, e.g., thermal denaturation and BIAcore surface-interaction techniques (Jensen, Biochemistry 36 (1997), 5072-5077). The synthesis of PNAs can be performed according to methods known in the art, for example, as described in Koch, J. Pept. Res. 49 (1997), 80-88; Finn, Nucleic Acids Research 24 (1996), 3357-3363. Furthermore, folding simulations and computer redesign of structural motifs of the CSFs and their receptors can be performed as described above to design drugs capable of inhibiting the biological activity of CSFs.

Furthermore, antibodies may be employed specifically recognizing CSF or their receptors or parts, i.e. specific fragments or epitopes, of such CSFs and receptors thereby inactivating the CSF or the CSF receptor. These antibodies can be monoclonal antibodies, polyclonal antibodies or synthetic antibodies as well as fragments of antibodies, such as Fab, Fv or scFv fragments etc. Antibodies or fragments thereof can be obtained by using methods which are described, e.g., in Harlow and Lane "Antibodies, A Laboratory Manual", CSH Press, Cold Spring Harbor, 1988 or EP-B1 0 451 216 and references cited therein. For example, surface plasmon resonance as employed in the BIAcore system can be used to increase the efficiency of phage antibodies which bind to an epitope of the CSF or its receptor (Schier, Human Antibodies Hybridomas 7 (1996), 97-105; Malmborg, J. Immunol. Methods 183 (1995), 7-13).

Putative inhibitors which can be used in accordance with the present invention including peptides, proteins, nucleic acids, antibodies, small organic compounds, ligands, hormones, peptidomimetics, PNAs and the like capable of inhibiting the biological activity of a CSF or its receptor may be identified according to the methods known in the art, for example as described in EP-A-0 403 506 or in the appended examples.

In a preferred embodiment, the agent which blocks the interaction of the CSF and its receptor is selected from the group consisting of (i) an anti-CSF antibody and an anti-CSF-receptor antibody; and/or (ii) a non-stimulatory form of a CSF protein and a soluble form of a CSF-receptor.

Such antibodies as well as inactive and soluble forms of CSFs and their receptors, respectively, are described in, e.g., Kogut, Inflammation 21 (1997) or in Shimamura, Journal of Histochemistry & Cytochemistry 38 (1990), 283-286 and can be obtained according to methods known in the art; see, e.g., supra.

In a preferred embodiment of the present invention, the agent is designed to be expressed in vascular cells or cells surrounding preexisting arteriolar connections to a tumor.

In a preferred embodiment, methods and uses of the invention are employed for the treatment of a tumor which is a vascular tumor, preferably selected from the group consisting of Colon Carcinoma, Sarcoma, Carcinoma in the breast, Carcinoma in the head/neck, Mesothelioma, Glioblastoma, Lymphoma and Meningeoma.

In a preferred embodiment, the pharmaceutical composition in the use of the invention is designed for administration by catheter intraarterial, intravenous, intraperitoneal or subcutenous routes. In the examples of the present invention the CSF protein was administered locally via osmotic minipump.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, e.g. under the U.S. National Library of Medicine web site. Further databases and web sites, such as the National Center for Biotechnology Information, Resources Centre INFOBIOGEN, the Friedrich Miescher Institute, and the Institute of Genomic Research, are known to the person skilled in the art and can also be obtained using, e.g., the Lycos web site. An overview of patent information in biotechnology and a survey of relevant sources of patent information useful for retrospective searching and for current awareness is given in Berks, TIBTECH 12 (1994), 352-364.

The use and methods of the invention can be used for the treatment of all kinds of diseases hitherto unknown as being related to or dependent on the modulation of neovascularization and/or the growth of collateral arteries and/or other arteries from preexisting arteriolar connections. The methods and uses of the present invention may be desirably employed in humans, although animal treatment is also encompassed by the methods and uses described herein.

The examples illustrate the invention.

EXAMPLE 1

Femoral Artery Occlusion of Animals and Local Delivery of Agents

The present study was performed with the permission of the State of Hessen, Regierungspräsidium Darmstadt, according to section 8 of the *German Law for the Protection of Animals*. It confirms with the *Guide for the Care und Use of Laboratoy Animals* published by the US National Institut of Health (NIH Publication No. 85-23, revised 1985).

6 rabbits were subjected to 7 days of right femoral artery occlusion. They were randomly assigned to either receive GM-CSF (Novartis, Nuernberg, Germany) (2ML-2, Alza Corp; 3 µg in 2 mL PBS at a rate of 10 µL/h) or PBS locally via osmotic minipump. For the initial implantation of the osmotic minipumps, the animals were anesthetized with an intramuscular injection of ketamine hydrochloride (40 to 80 mg/kg body weight) and xylazine (8 to 9 mg/kg body weight). Supplementary doses of anesthetic (10% to 20% of the initial dose) were given intravenously as needed. The surgical procedure was performed under sterile conditions. Femoral arteries were exposed and cannulated with a sterile polyethylene catheter (inner diameter: 1 mm; outer diameter: 1,5 mm) pointing upstream, with the tip of the catheter positioned distal to the branching of the arteria circemflexa femoris. The catheter itself was connected to the osmotic minipump (2ML-2, Alza Corp), which was implanted under the skin of the lower right abdomen. After that the animals were outfitted with a specially designed body suit that allowed them to move freely but prevented self-mutilation. The rabbits were housed individually with free access to water and chow to secure mobility. The body weights and body temperature in rabbits treated with GM-CSF did not significantly differ from those of control rabbits. Serum values of total protein, albumin, glutamic oxaloacetic transaminase, and glutamic pyruvic transaminase were not significantly changed by the GM-CSF treatment.

Seven days after implantation the animals were again anasthetized with an intramuscular injection of ketamine hydrochloride and xylazine for tracheostomy and artificial ventilation. Anesthesia was deepened with pentobarbital (12 mg/kg body weight per hour). The carotid artery was cannulated for continuous pressure monitoring. The arteria saphena magna (anterior tibial artery in humans and main arterial supply to the lower limb and foot in the rabbit) was exposed just above the ankle and cannulated with sterile polyethylene heparinized tubing (inner diameter 0,58 mm; outer diameter 0,9 6 mm). They were connected to a Statham P23DC pressure transducer (Statham, Spectramed) for measurement of peripheral pressures (PP). After heparinization with 5000 Units heparin, the left femoral artery was exposed and cannulated with sterile polyethylene catheter (inner diameter: 1 mm; outer diameter: 1,5 mm) for the microsphere reference sample. After cannulation of the abdominal aorta a shunt was installed to ensure oxygenated blood flow from the carotid artery via the canula in the abdominal aorta into the right and left legs. A flow probe was installed to measure total flow to both hindlimbs.

EXAMPLE 2

Ex Vivo Pressure-flow Relations

Maximum vasodilation was achieved by injecting 20 mg papaverine (Sigma) to the shunt at a flow rate of 20 ml/min. After stabilization of peripheral and central pressures both legs were perfused via four different pressure. Each pressure gradient was combined with a bolus of microspheres.

Five different perfusion pressures (30, 40, 50, 60, 80 mmHg) were generated in vivo with a roller pump installed in the above mentioned shunt between carotid artery and abdominal aorta. Peripheral pressures and collateral flows were measured under maximal vasodilation (papaverine) using Statham pressure transducers.

For each pressure level microspheres with a different fluorescent color (either crimson, scarlett, blue-green, red or blue) were injected into the mixing chamber, which was installed in the carotid-abdominal aortic shunt.

The following muscles were dissected from the leg: Quadriceps, adductor longus, adductor magnus, gastrocnemius, soleus, and peroneal muscles. Each muscle was divided into 3 three consecutive samples from the proximal to the distal end. The whole muscle and afterwards each sample were weighed and cut to small pieces.

The muscle sample were then placed loosely into 12 mm×75 mm polystyrene tubes (Becton Dickinson & Co, Lincoln Park, N.J.) and 3 ml of SDS solution [SDS solution (Boehringer Mannheim Corp.): 1% SDS (Boehringer Mannheim Corp.), 0,5% sodium azide (Sigma Chemical Company, St. Louis, Mo.), and 0,8% Tween-80 (Fisher Scientific, Fairlawn, N.J.) in 50 millimolar pH 8 tris buffer (Sigma Chemical Company, St. Louis, Mo.)], 30 µl proteinase K solution (Boehringer Mannheim Corp.) and 1 ml of microspheres as internal standard was added (13,7 µm, Fluorescein Kit, Flow Cytometry Standards, Corp. San Juan, P.R.). Each tube was capped and secured in a shaking water bath for 24-48 hours. The samples were then subsequently spinned at 1000 g for 45 minutes, the supernatant was pipetted off and the pellet was resuspended in 1 ml PBS (pH 7.4). Before FACS analysis the probes were rigorously shaken. The microspheres were counted using a flow cytometer (FACS-Calibur) equipped with a second laser and a detector for a fourth fluorescence. Flows for each sample were calculated from the number of microspheres in the sample ($m^s$), the respective microspheres count in the reference sample ($m^{rs}$), the internal standard in the sample (ISs), internal standard in the reference sample (IS rs), the weight of the reference sample (W) and the time during which the reference sample was withdrawn using following equation.

$$\text{flow [mg/ml]} = \frac{m^s \cdot IS^s}{IS^s \cdot m^{rs}} \cdot \frac{w}{t}$$

$m^s$=sample microsphere
$IS^{rs}$=internal standard reference sample
$IS^s$=internal standard sample
$m^{rs}$=microsphere reference sample
w=weight
t=time In the present model, collateral arteries developing after femoral artery occlusion in typical corkscrew formation supply blood to the distal adductor region and the lower leg. The systemic pressure [SP] and peripheral pressure [PP] was measured.

Venous pressure was equal to atmospheric pressure [AP] (zero in the present case). Since arterial resistances are much lower than collateral and peripheral resistances, they can be neglected. SP represent the pressure at the stem region of the collateral arteries. PP is the pressure at the reentry region and is identical to the pressure head of the circulation in lower leg; AP, the pressure at the venous end of the peripheral circulation. Collateral flow is equal to the sum of flow to the tissue of the distal adductor plus the flow to the tissue of the lower leg. Collateral resistance was defined as pressure difference between SP and PP divided by the flow going to the distal adductor an the lower leg. Peripheral resistance was defined as PP divided by flow to the lower leg, and bulk conductance was defined as SP divided by bulk flow recorded with the ultrasonic flow probe. The reciprocal values of these resistances represent collateral, peripheral, and bulk conductance. Because a positive pressure intercept is observed event at maximal vasodilation, all conductances were calculated from the slope of pressure-flow relations. Data are described as mean±SD. Differences among data were assessed using unpaired Student's t-test for intergroup comparisons and Mann-Whitney rank-sum test for unequal variances. Values of $p \leq 0.05$ were required for assumption of statistical significance. Collateral conductance was significantly higher after 1 week of occlusion in animals treated with GM-CSF compared with animals without this treatment.

TABLE 1

| | collateral conductance [ml/min/100 mmHg] | | |
|---|---|---|---|
| | GM-CSF | PBS | p |
| mean | 68.685 | 21.101 | 0.001 |

EXAMPLE 3

Post Mortem Angiography

Legs were perfused with Krebs-Henseleit buffered saline in a warmed waterbath of 37° C. for 1 minute at a pressure of 80 mmHg, followed by perfusion with contrast medium (8 to 10 minutes at 80 mmHg) based on bismuth and gelatin according to a formula developed by Fulton (Fulton: The Coronary Arteries, Thomas Books, 1965). Subsequently, the contrast medium was allowed to gel by placing the limbs on crushed ice for 45 minutes. Angiograms were taken at two different angles in a Balteau radiography apparatus (Machlett Laboratories) using a single-enveloped Structurix D7DW film (AGFA). The resulting stereoscopic pictures allowed analysis of collateral growth in three dimensions.

To differentiate between collateral vessels and muscle vessels for further quantification, Longland's definition of collateral arteries was used (Longland et.al. 1954 "Description of collateral arteries" Verlag: Thomas). Stem, midzone and re-entry were identified under stereoscopic viewing using a 3-fold magnification of our angiograms. Collateral arteries then were divided in two groups: group one consisted of vessels whose stem branched from the Arteria circumflexa femoris lateralis. Group two of the arteries originated from the Arteria profunda femoris. The length of the midzone in each group was almost the same, so their measurement did not give any further information. Re-entry of the collaterals from the first group usually descended into the Arteria genus descendens, the second group into the Arteria caudalis femoris. Only about 10% of the collateral arteries originate from other vessels, e.g from the A. iliaca externa or from the A. iliaca interna.

Figure 1:
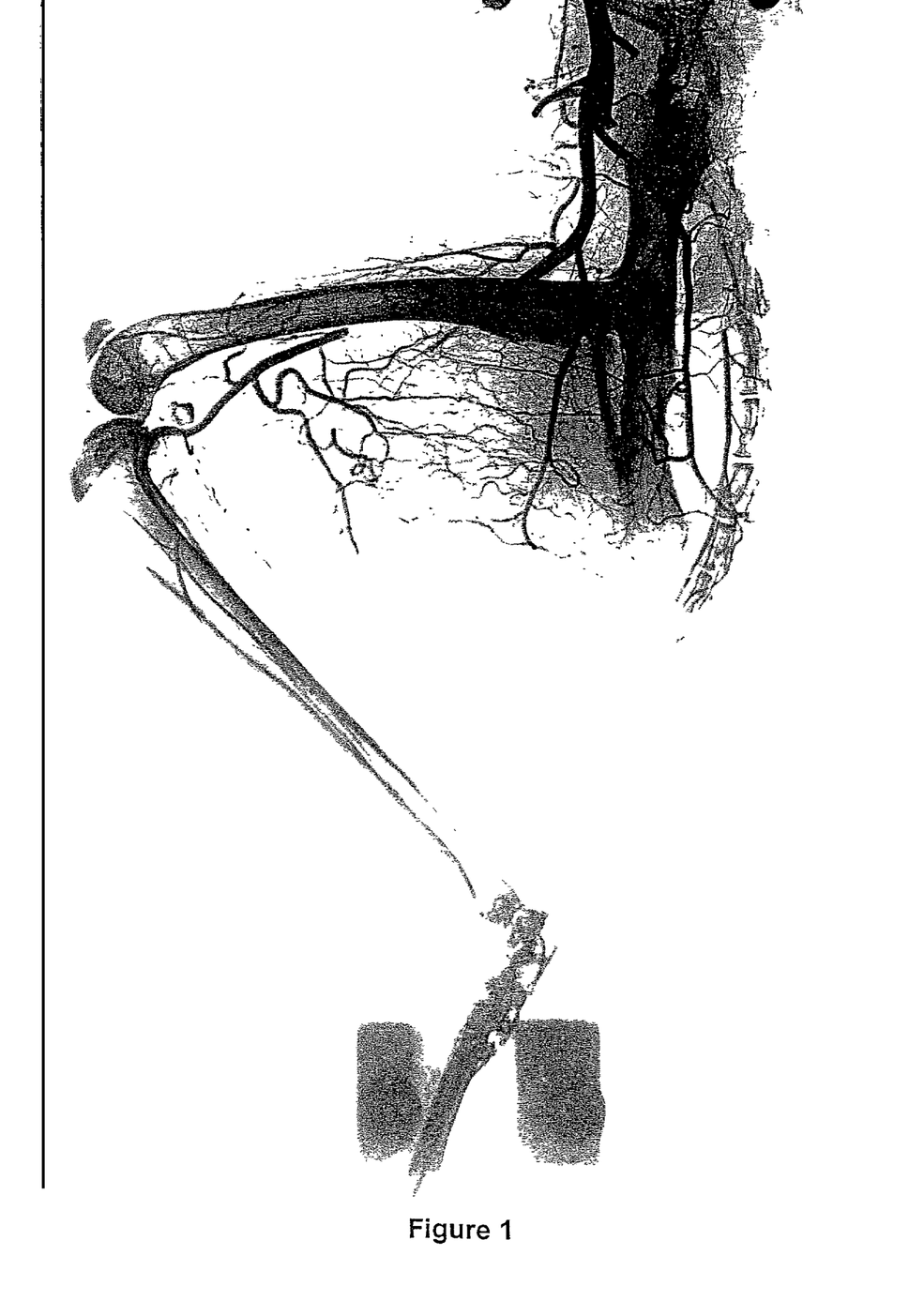
FIG. 1: Angiography of the whole right leg of an animal treated with GM-CSF.
Figure 2A:
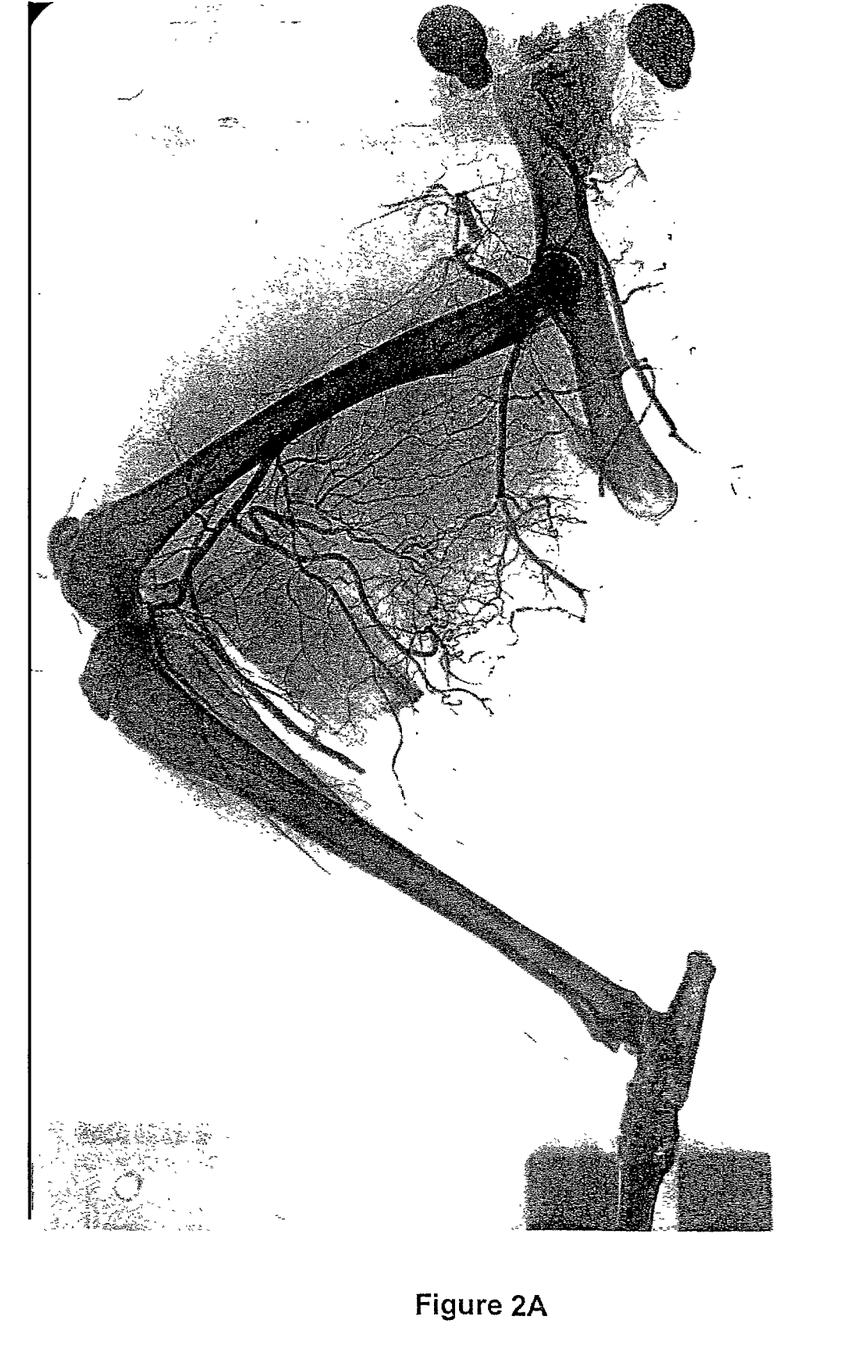
FIGS. 2A and 2B: Angiography of the whole right leg (FIG. 2A) and of the collateral circulation (FIG. 2B) (without Os femoris) of an animal treated with GM-CSF.
Figure 2B:
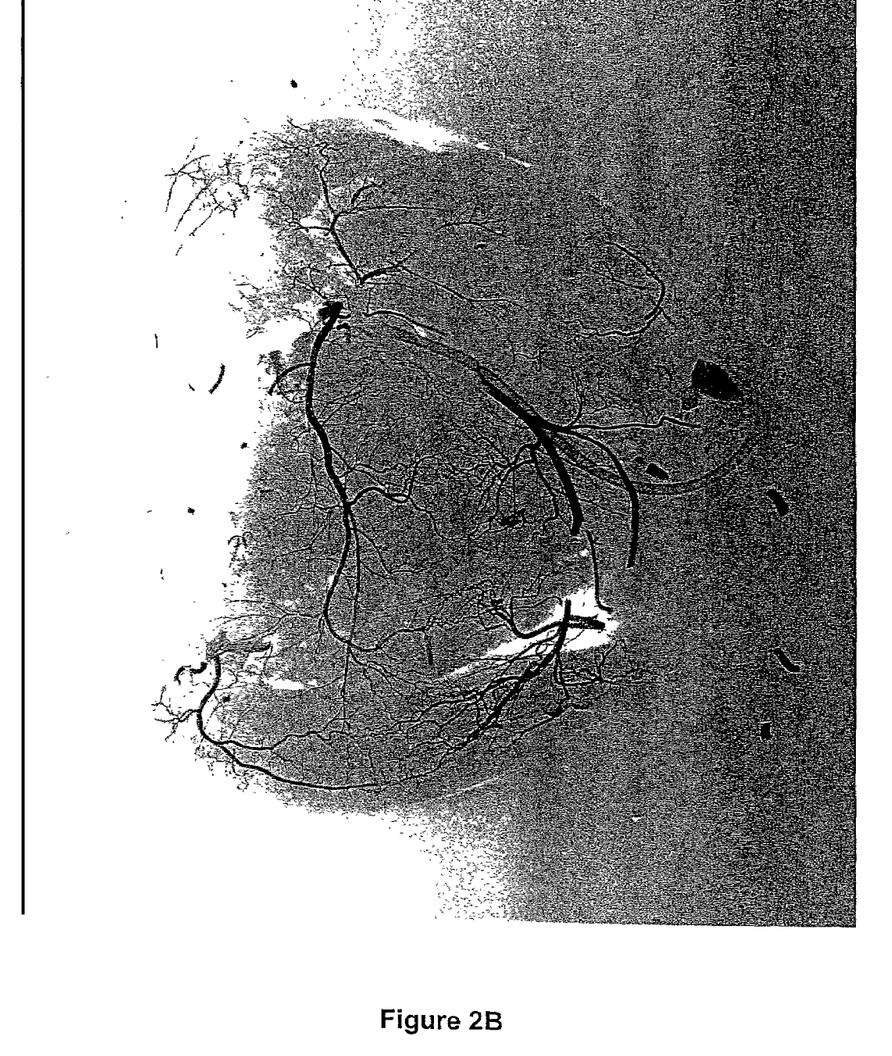
Figure 3:
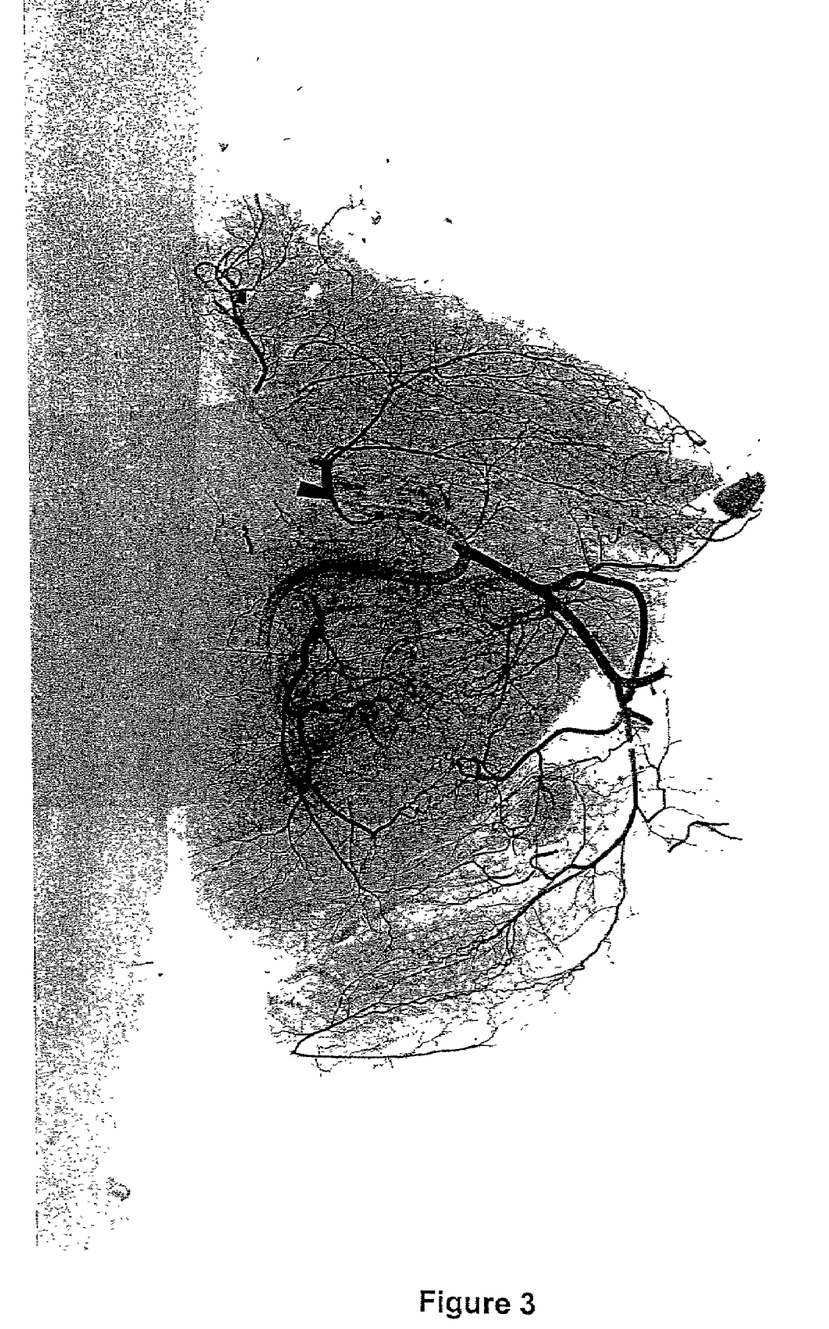
FIG. 3: Angiography of the collateral circulation (without Os femoris) of an animal treated with GM-CSF.
Figure 4:
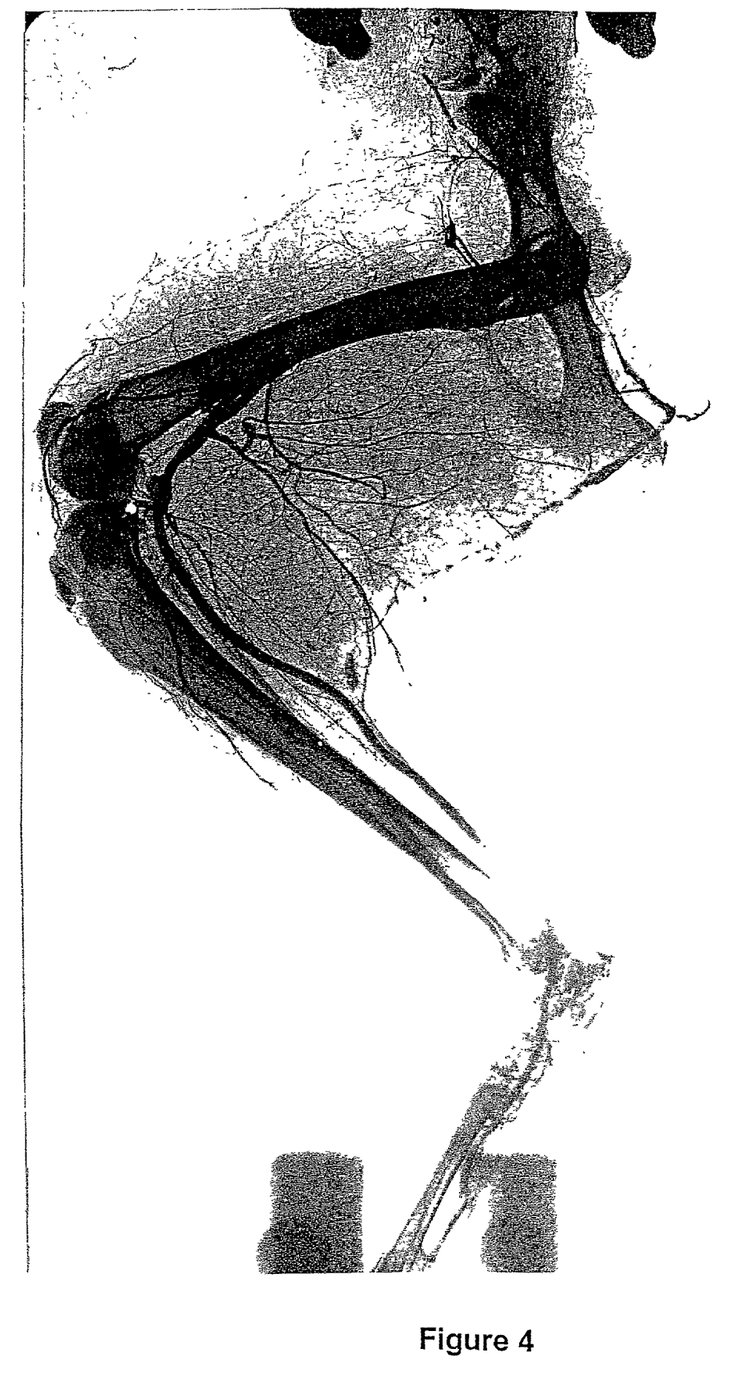
FIG. 4: Angiography of the whole right leg of an animal treated with PBS.
Figure 5:
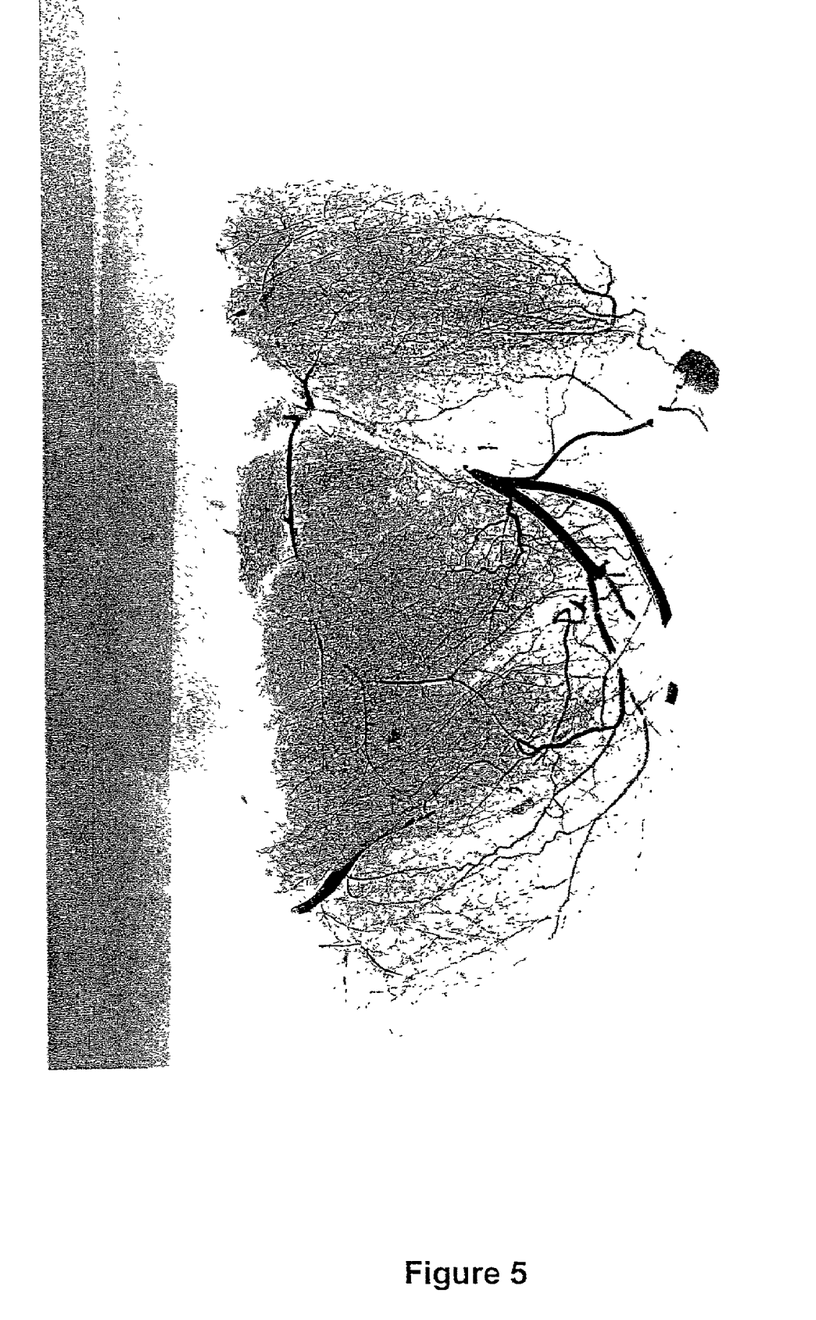
FIG. 5: Angiography of the collateral circulation (without Os femoris) of an animal treated with PBS.

Collateral vessels were marked after counting to make sure, that no vessel was counted twice. A further 3-fold magnification was used to measure the diameter of the vessels with an accuracy of 0.1 mm. Postmortem angiograms exhibited corkscrew collaterals mainly in the adductor longus, adducotr magnus, and vasuts intermedius connecting the perusion bed of the arteria femoralis profunda to that of the arteria saphene parva int the adductor muscles and the perfusion bed of the arteria circumflexa femoris lateralis to that of the arteriae genuales in the quadriceps muscle. Angiograms taken from hindlimsb of animals treated with GM-CSF show a remarkable increase the diameter and density of these collateral vessels. (Table 2, FIGS. 1 to 5)

TABLE 2

| | Number of collateral arteries | | |
|---|---|---|---|
| | GM-CSF | PBS | p |
| mean | 26 | 14 | 0.02 |

The results of the experiments performed in accordance with the present invention indicate that CSFs are capable of mediating neovascularization and/or collateral artery growth and/or growth of arteries from preexisting arteriolar connections due to macrophage recruitment that might be mediated by a direct effect of CSFs on macrophage activation, proliferation, motility, and survival and, secondarily, by chemoattractant molecules released in response to locally administered CSFs. Thus, the present invention provides for novel means and methods for the treatment of diseases which depend on neovascularization and/or collateral artery growth.

The present invention is not to be limited in scope by its specific embodiments described which are intended as single illustrations of individual aspects of the invention and any proteins, nucleic acid molecules, or compounds which are functionally equivalent are within the scope of the invention. Indeed, various modifications of the invention in addition to those shown and described therein will become apparent to those skilled in the art from the foregoing description and accompanying drawings. Said modifications intended to fall within the scope of the appended claims. Accordingly, having thus described in detail preferred embodiments of the present invention, it is to be understood that the invention defined by the appended claims is not to be limited to particular details set forth in the above description as many apparent variations thereof are possible without departing from the spirit or scope of the present invention.

The invention claimed is:

1. A method of treating an arterial occlusion in a human stroke patient, said method consisting of:
   (a) identifying a human patient with a stroke;
   (b) administering to said patient a pharmaceutical composition consisting of a G-CSF protein and a pharmaceutically acceptable carrier or excipient in an amount effective to enhance the growth of arteries in said patient by proliferation of endothelial and smooth muscle cells from preexisting arteriolar connections; and
   (c) treating said arterial occlusion in said patient by enhancing said growth of said arteries from said preexisting arteriolar connections in said patient as a result of said administering.

2. The method of claim 1, wherein said G-CSF protein is a recombinant G-CSF.

3. The method of claim 1, wherein said pharmaceutical composition is administered by an intracoronary, intramuscular, intraarterial, intravenous, intraperitoneal or subcutaneous route.

4. The method of claim 3, wherein said pharmaceutical composition is administered by the intravenous route.

5. A method of treating an arterial occlusion in a human stroke patient, said method consisting of:
   (a) identifying a patient with a stroke;
   (b) administering to said patient a pharmaceutical composition consisting of a G-CSF protein, a protein growth factor, and a pharmaceutically acceptable carrier or excipient in an amount effective to enhance the growth of arteries in said patient by proliferation of endothelial and smooth muscle cells from preexisting arteriolar connections; and
   (c) treating said arterial occlusion in said patient by enhancing said growth of said arteries from said preexisting arteriolar connections in said patient as a result of said administering.

6. The method of claim 5, wherein said pharmaceutical composition is administered by an intracoronary, intramuscular, intraarterial, intravenous, intraperitoneal or subcutaneous route.

7. The method of claim 6, wherein said pharmaceutical composition is administered by the intravenous route.

8. The method of claim 1, wherein said arterial occlusion is a cerebral occlusion.

9. The method of claim 5, wherein said arterial occlusion is a cerebral occlusion.

* * * * *